(12) United States Patent
Lacaze

(10) Patent No.: US 11,426,222 B2
(45) Date of Patent: Aug. 30, 2022

(54) OSSEOUS ANCHORING IMPLANT WITH OPTIMIZED EXPANSION

(71) Applicant: LOCK IN SA, Rolle (CH)

(72) Inventor: Guillaume Lacaze, La Rippe (CH)

(73) Assignee: LOCK IN SA, Rolle (CH)

( * ) Notice: Subject to any disclaimer, the term of this patent is extended or adjusted under 35 U.S.C. 154(b) by 22 days.

(21) Appl. No.: 17/094,298

(22) Filed: Nov. 10, 2020

(65) Prior Publication Data

US 2021/0315619 A1  Oct. 14, 2021

(30) Foreign Application Priority Data

Apr. 9, 2020 (FR) .................................. 2003577

(51) Int. Cl.
*A61B 17/84* (2006.01)
*A61B 17/86* (2006.01)
*A61B 90/00* (2016.01)

(52) U.S. Cl.
CPC ........ *A61B 17/844* (2013.01); *A61B 17/8625* (2013.01); *A61B 17/8685* (2013.01); *A61B 90/39* (2016.02)

(58) Field of Classification Search
CPC ........................... A61B 17/8685; A61B 17/844
See application file for complete search history.

(56) References Cited

U.S. PATENT DOCUMENTS

2008/0039846 A1\* 2/2008 Lee ...................... A61B 17/686
433/7

FOREIGN PATENT DOCUMENTS

EP         2603163 A1   6/2013
WO    2012045787 A1   4/2012

\* cited by examiner

*Primary Examiner* — Olivia C Chang
(74) *Attorney, Agent, or Firm* — Hauptman Ham, LLP

(57) ABSTRACT

An osseous anchoring implant with optimized expansion, having a tubular body and a rod whose external profile of the rod and internal profile of the tubular body are complementary. The implant being expandable between a rest configuration in which an abutment mechanism interlocks the tubular body and the rod thanks to the reversal of their two respective screw pitches, so that they provide in an expanded configuration radially: a proximal bearing point, a distal bearing point, a "central" bearing point located between these two bearing points, formed by the cooperation between the outer diameter of the rod and the inner diameter of the tubular body which induce an outer diameter of the tubular body at the "central" level greater than the outer diameter of the tubular body at the proximal bearing point.

21 Claims, 7 Drawing Sheets

[Fig. 1a]
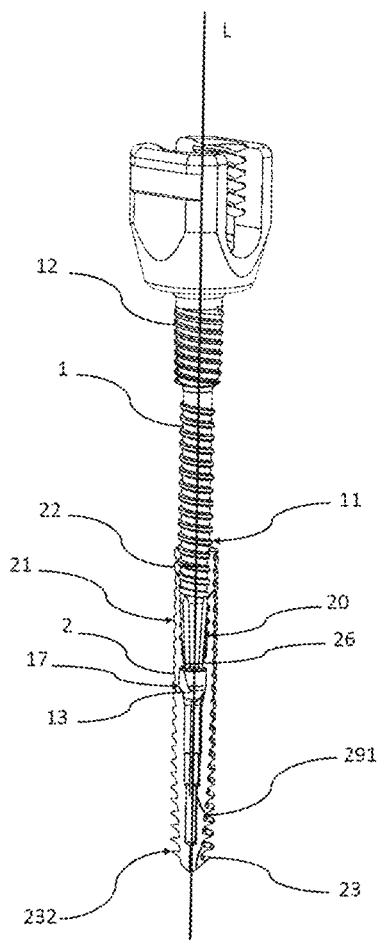

[Fig. 1b]
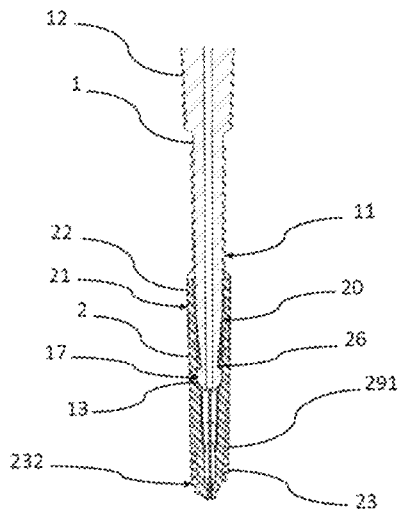
[Fig. 2]
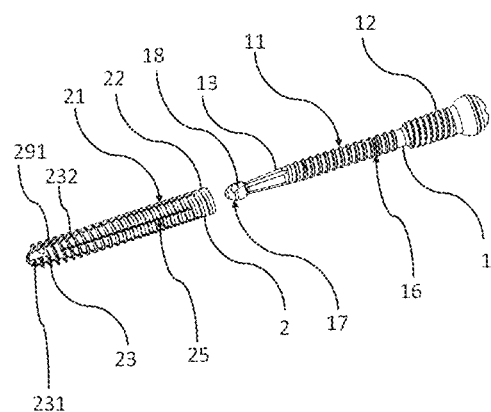
[Fig. 3a]
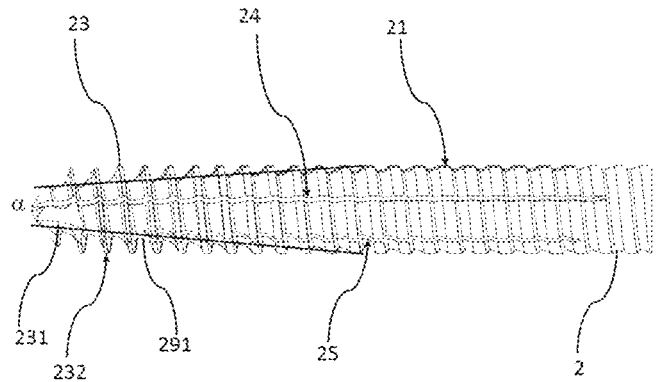

[Fig. 3b]
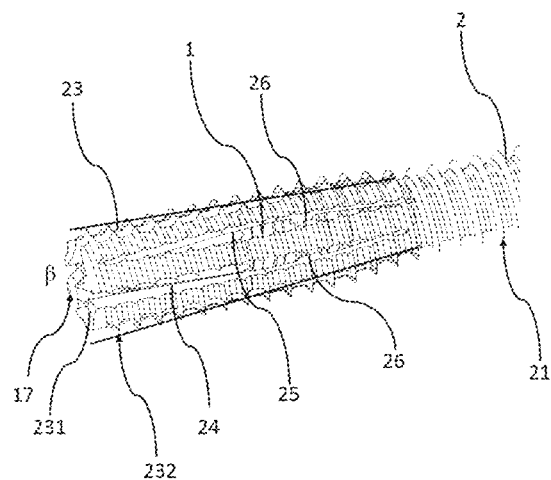
[Fig. 3c]
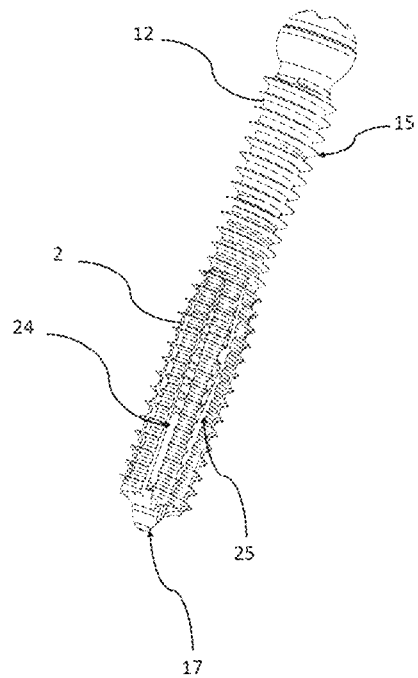

[Fig. 4a]
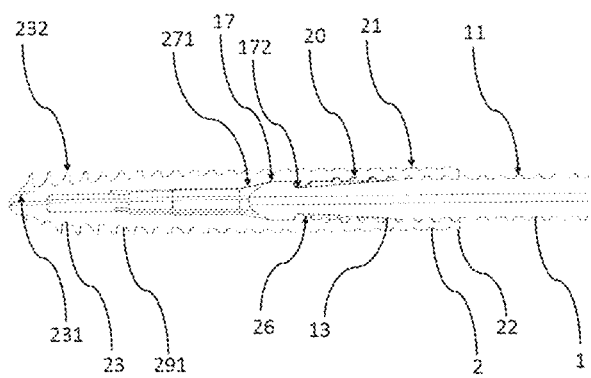
[Fig. 4b]
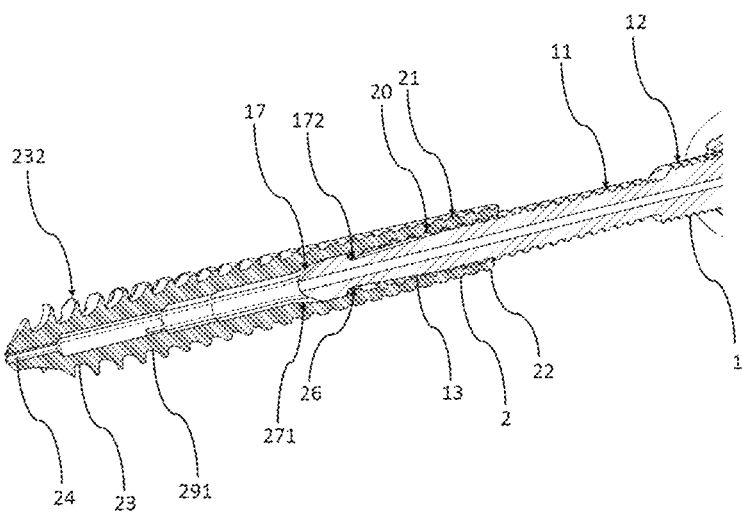

[Fig. 5a]
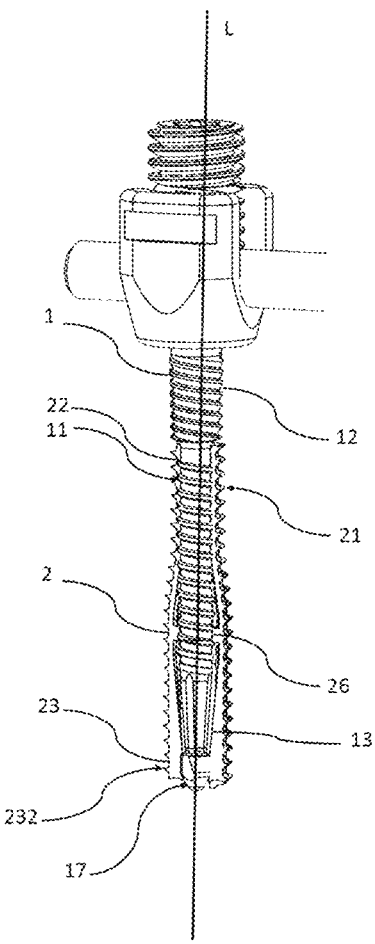
[Fig. 5b]
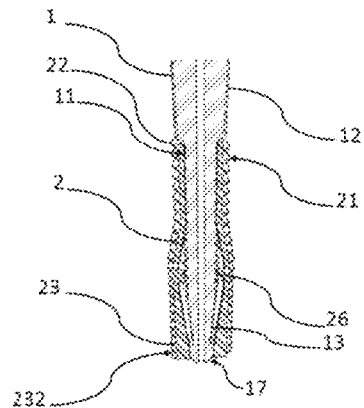

[Fig. 6]
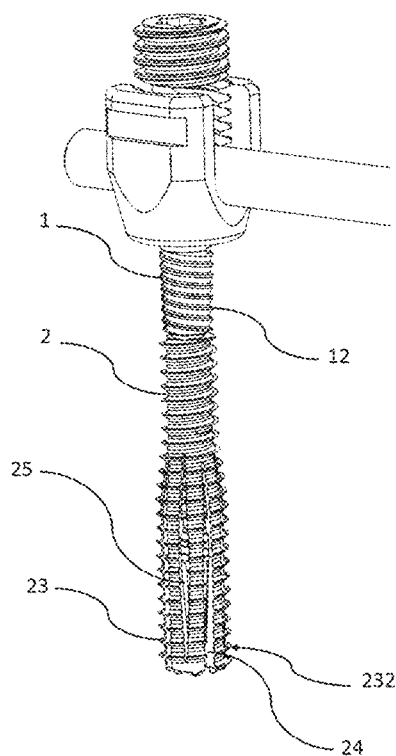
[Fig. 7]
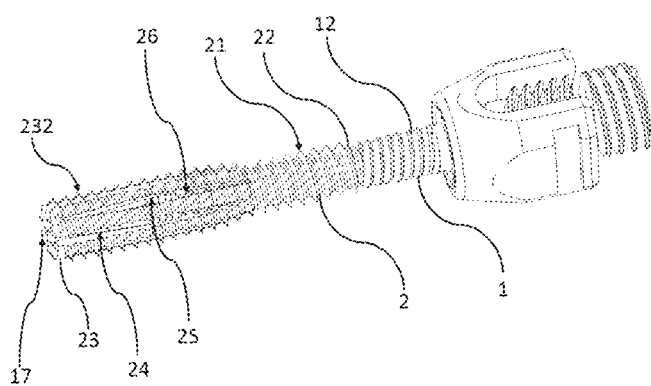

[Fig. 8]
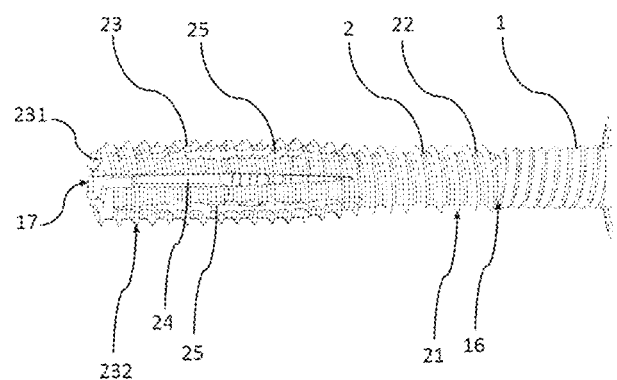
[Fig. 9]
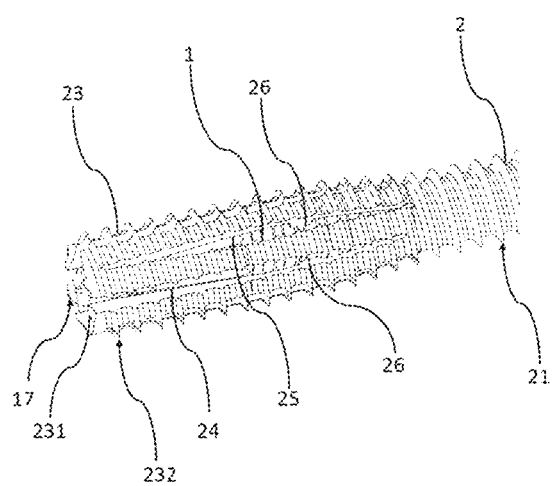
[Fig. 10]
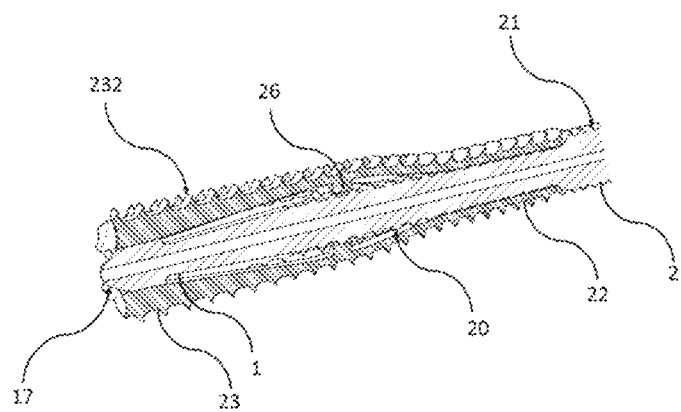

OSSEOUS ANCHORING IMPLANT WITH OPTIMIZED EXPANSION

RELATED APPLICATIONS

The present application claims the priority of French Application No. 2003577, filed Apr. 9, 2020, which is incorporated herein by reference in its entirety.

TECHNICAL FIELD AND OBJECT OF THE INVENTION

The present invention relates to the field of osseous implants for dental, orthopedic, surgical or osteoplastic applications, such as orthopedic screws alone or with plates, dental or ligament implants for joints such as for example the hips, the elbows, the ankles, the shoulders and the knees, or rachidian spinal implants for example for the vertebrae. These fields of application are given by way of example and are not restrictive as to the scope of the present invention.

More specifically, the invention relates to an osseous implant whose implantation in the osseous tissue is stabilized by expansion, in particular in the cancellous part of the bone.

STATE OF THE ART

An osseous anchoring implant generally consists of an elongate body intended to be implanted in a housing formed in an osseous tissue, such as the jaw bone for a dental application or in a vertebra for example.

It is important that the osseous anchoring implant can be easily introduced into the osseous tissue, without creating damage, and that the anchoring device inside the osseous tissue is stable. Indeed, current osseous implant devices do not allow reliable anchoring without generating more cracks or damage than required for the size of the device itself in the osseous tissue. It is necessary that the fixation in the osseous anchoring implant is reliable and stable, because many therapeutic techniques today rely on bone growth that generally requires that the devices anchored in the osseous tissue remain as immobile as possible.

In addition, it is also necessary that the implantation in the osseous tissue is easy to perform in order to avoid any risk of incorrect positioning of the osseous anchoring implant, which could in particular be due to a difficulty in the positioning or in the implantation in the bone.

The state of the art comprises the patent document EP2603163 B1, which describes an endosseous implant with improved anchoring able to be implanted in an osseous tissue and including a fixing device comprising a part called gripping part in the osseous tissue, and a part called expansion part, these two parts being movable relative to each other. The invention mentioned in this patent also comprises cooperating mechanical connection means disposed, on the one hand, on the gripping part and, on the other hand, on the expansion part, so that the relative mobility of the two parts comprises at least one degree of freedom and that a relative displacement of said two parts causes a widening of the gripping part, said widening causing the anchoring of the gripping part in the osseous tissue. The osseous implant described in this patent particularly finds application in the dental field.

However, such a solution has drawbacks because the proposed osseous implant has a conical portion only on its distal portion which opens on through-slots. The expansion of the osseous implant in the osseous tissue then occurs in a radial and homothetic manner which makes it less stable in particular when it is removed from the osseous tissue which firstly causes the osseous implant to recede before it can be removed.

The invention therefore aims at solving these drawbacks by proposing an osseous implant able to be implanted and immobilized in the osseous tissue in a stable manner.

GENERAL PRESENTATION OF THE INVENTION

The present invention therefore aims at overcoming the drawbacks of the prior art by proposing an osseous anchoring implant, hereinafter called osseous implant, which is easily implantable in the osseous tissue, stable and also easily removable from the osseous tissue.

To achieve this result, the present invention relates to an osseous anchoring implant with optimized expansion, comprising:

A tubular body extending between a proximal portion having a first internal diameter, and a distal portion having a second internal diameter smaller than said first internal diameter, these two portions defining a longitudinal axis (L) and said first and second internal diameters defining an internal profile of said tubular body, and comprising, on the one hand, at least a first threading inside the tubular body and, on the other hand, at least a second threading outside the tubular body, A rod extending between a proximal portion and a distal portion on an axis collinear with the axis (L) and having, on the one hand, along said longitudinal axis (L), an external profile complementary to said internal profile of said tubular body and, on the other hand, at least one external threading whose screw pitch is reversed relative to said second external threading of the tubular body, The implant being expandable between, on the one hand, a rest configuration in which an abutment mechanism interlocks said tubular body and said rod thanks to the reversal of these two screw pitches and, on the other hand, an expanded configuration obtained by the actuation of said complementary internal and external threadings of the tubular body and of the rod mutually, causing the penetration of the rod into the tubular body and generating the expansion of said tubular body, thanks to the external diameter of the rod which is greater than the internal diameter of the tubular body, at least on a distal portion, by deformation of the tubular body during penetration of the rod into the tubular body, The external profile of the rod and the internal profile of the tubular body being complementary, so that they provide, in an expanded configuration:

A proximal bearing point supported by the complementarity of the outer diameter of the rod with the inner diameter of the tubular body, A distal bearing point supported by the cooperation between the tubular body whose inner diameter narrows towards the distal portion until becoming smaller than the outer diameter of the rod, A "central" bearing point located between these two bearing points, formed by the cooperation between the outer diameter of the rod and the inner diameter of the tubular body which induce an outer diameter of the tubular body at the "central" level which is greater than the outer diameter of the tubular body at the proximal bearing point.

According to one feature, the proximal bearing point is formed on at least one portion of the distal portion complementary to the external profile of the rod.

According to another feature, the distal bearing point is formed by said distal portion comprising a tip whose external profile is complementary to the internal profile of the distal portion of the tubular body.

According to another feature, the central bearing point is formed on an intermediate portion located between the distal portion and the proximal portion whose internal profile is complementary to the external profile of the rod.

According to another feature, the mutual abutment mechanism includes a rib protruding inside the tubular body complementary to a shoulder or to a cut located on the tip of the rod.

According to another feature, the central bearing point includes a rib or a shoulder or a protrusion inside the tubular body, complementary to the external diameter of the rod, or a rib on the inside of the tubular body, complementary to a groove or to a shoulder on the rod.

According to another feature, the central bearing point and the abutment mechanism interlocking the tubular body and the rod are formed by the same structure.

According to another feature, the external diameter of the rod is greater than the internal diameter of the tubular body, by at least one narrowing on a distal portion.

According to another feature, said at least one narrowing is located separate from the proximal portion by a distance determined as a function of the thickness of the depth at which said expansion is desired.

According to another feature, the tubular body comprises on its distal portion a frustoconical portion whose internal diameter is smaller than the external diameter of the rod.

According to another feature, the frustoconical portion has a threading with a conical core allowing the tubular body to sink deep into the bone.

According to another feature, the distal portion includes self-tapping notches.

According to another feature, the distal portion includes longitudinal through-slots allowing the expansion of the tubular body.

According to another feature, there are as many self-tapping notches as there are longitudinal through-slots.

According to another feature, the distal portion includes longitudinal non-through slots allowing the expansion of the tubular body.

According to another feature, the rod comprises at least one distance marker to visualize the moment when the screwing of the rod in the tubular body must be carried out in the opposite direction to the screwing of the tubular body in the osseous tissue.

According to another feature, said at least one distance marker is a laser marker.

The invention also relates to a method for placing an osseous implant comprising an osseous implant as briefly described above, the method comprising the following steps:

Screwing the osseous implant in the direction of the external threading until the distance marker is flush with the surface of the bone cortex, Screwing the osseous implant by screwing in the direction of the second threading to complete the screwing of the body of the threaded rod into the bone and to proceed with the expansion of the tubular body.

According to one feature, the cortical bone is perforated by means of a cortical preform tool.

The invention also relates to a method for extracting an osseous implant comprising an osseous implant as briefly described above, the method comprising the following steps:

Unscrewing the osseous implant in the direction of the external threading until the appearance of a distance marker, Locking the implant by a clamp blocking the rod in the tubular body in the rest position, Unscrewing the implant in the direction of the second threading.

According to one feature, the extraction method comprises an additional screwing before unscrewing the osseous implant.

PRESENTATION OF THE FIGURES

Other characteristics and advantages of the invention will appear upon reading the detailed description of the embodiments of the invention, given by way of example only, and with reference to the drawings which show:

FIG. 1a, FIG. 1b and FIG. 2 represent a detailed view of the elements that make up the osseous implant according to the invention.

FIG. 3a represents a detailed view of the tubular body before the expansion according to the invention.

FIG. 3b and FIG. 3c represent a detailed view of the tubular body after the expansion according to the invention.

FIG. 4a and FIG. 4b represent a diagram of a section of the interior of the rod penetrating into the tubular body at the mutual abutment, according to the invention.

FIG. 5a and FIG. 5b represent a diagram of a view of the interior of the osseous implant in the expanded position according to the invention.

FIG. 6 and FIG. 7 represent a view of the exterior of the osseous implant in the expanded position according to the invention.

FIG. 8 and FIG. 9 represent a view of the expanded tubular body according to the invention.

FIG. 10 represents a diagram of a section of the interior of the tubular body comprising the rod, in the expanded position, according to the invention.

DETAILED DESCRIPTION OF ONE EMBODIMENT OF THE INVENTION

Various embodiments of the invention are described below in particular with reference to the illustrative and non-limiting figures.

The present application relates to the implantation of an osseous implant in an osseous tissue.

It should be noted here that the term "implantation" designates the fact of introducing the osseous implant into the osseous tissue, generally by screwing. The implantation proposed in the present application designates a sufficiently solid and stable introduction of the osseous implant to ensure good maintenance of this osseous implant in the osseous tissue.

In addition, the term "osseous tissue(s)" generally designates all types of bones, whether they are compact bones (such as the cortical bone or the periosteum) or cancellous (soft, porous) bones, because the osseous implant system of the present application is implantable in any type of osseous tissue.

In addition, the terms used should not be interpreted in their general meaning but rather in the light of the functional considerations detailed in the present application.

FIG. 1a, FIG. 1b and FIG. 2 are illustrative and non-limiting exemplary embodiments of the osseous implant.

As for example represented in FIG. 1a, FIG. 1b and FIG. 2, an osseous implant comprises: a tubular body (2) extending along a longitudinal axis (L) between a proximal portion (22) and a distal portion (23) which comprises, on the one hand, at least a first threading (20) inside the tubular body (2) and, on the other hand, at least a second threading (21) outside the tubular body (2).

In the present application, the term "tubular body (2)" generally designates a hollow generalized cylinder.

In some embodiments, the osseous implant also comprises a rod (1) also extending along said longitudinal axis (L) between a proximal portion (12) and a distal portion (13) and having, on the one hand, along said longitudinal axis (L), an external profile complementary to the internal profile of said tubular body (2) and, on the other hand, at least one external threading (11) whose screw pitch is reversed relative to said second external threading (21) of the tubular body (2).

The terms "proximal" and "distal" designate in the present application, respectively, the part where the implantation device is held to allow its implantation in the osseous tissue, and the part which is implanted first in the osseous tissue (opposite the proximal portion).

The terms "proximal and distal portions" designate in the present application the parts located in the vicinity of the distal and proximal ends. In some embodiments, the proximal portion (12) of the rod (1) is directly implanted in the cortical bone.

In some embodiments, the proximal end of the rod (1) comprises an actuating means making it possible to screw the rod (1), said actuating means comprising a structure of any shape desirable by the practitioner depending on the use which will be made of it, as for example represented in FIG. 1*a*. The actuating means being for example a hexagonal hole or a torx or a cruciform or any other actuating means, and the proximal end of the rod (1) may have various shapes depending on the desirable destination for the osseous anchoring implant (head for fixing a polyaxial or non-polyaxial osteosynthesis bar, or for fixing a plate or any other device).

In some embodiments, the rod (1) comprises a cannula passing through the rod (1) to allow the practitioner to inject for example cement, if he considers it necessary.

In some embodiments, the second threading (21) outside the tubular body (2) allows osseous anchoring. The term "osseous anchoring" used in the present application generally designates various types of devices comprising at least one element intended to enter the osseous tissue along a rectilinear path, under the action of a push generally exerted in the form of repeated screwing operations, impacts or strikes. It is known that an osseous anchoring threading has a thread height generally greater than that of a mechanical threading to ensure better anchoring. In addition, an osseous anchoring threading is generally different from a mechanical threading and those skilled in the art know that, depending on the type of bone and desired application, it is possible to vary the diameter of the core, the screw pitch and the wire height and the present application covers these various embodiments.

In addition, in some embodiments, some mechanical threads, such as trapezoidal threads, offer less resistance which facilitates the penetration of the rod into the tubular body anchored in the bone. Indeed, a trapezoidal thread allows distributing a large load in compression and in tension, which improves the stability of the implant over time and whatever the conditions.

In some embodiments, the tubular body (2) comprises on its distal portion (23) a frustoconical portion (291) whose internal diameter is smaller than the external diameter of the rod (1).

In some embodiments, the frustoconical portion (291) has a threading (232) with a conical core allowing the tubular body (2) to sink deep into the bone.

In some embodiments, the distal portion (23) of the tubular body (2) is self-tapping and includes self-tapping (milling and tapping) notches (231), as for example represented in FIG. 3*a*, FIG. 3*b*, FIG. 4*a* and FIG. 4*b*. This distal portion (23) allows preserving the bone during the implantation while avoiding pre-drilling before insertion of the implant, and thus allows keeping a maximum amount of bone around the implanted area, which improves the stability of the osseous implant. Indeed, the osteointegration time is thus reduced, which limits the need to add any type of bone filling material, whether synthetic or natural. In addition, the distribution of the notches (231) ensures a good balance over each of the parts of the distal portion (23) and thus a good uniformity of the distribution of the force during the insertion of the implant into the osseous tissue.

In some embodiments, the rod (1) comprises at least one laser marker (16) serving as a positioning mark for the practitioner during the penetration of the osseous implant into the bone, as represented for example in FIG. 2.

It should be noted that the osseous implant is made of titanium or of implantable medical stainless steel or of polyetherketoneketone (PEKK) or of polyetheretherketone (PEEK) or any other material of which those skilled in the art can determine the suitability depending on its mechanical, physico-chemical properties and on its biocompatibility.

The present application also relates to a method for implanting an implant as described in the various embodiments of the present application.

In some embodiments, such a method comprises the following steps:

Screwing the osseous implant in the direction of the external threading (21) until the laser marker (16) is flush with the surface of the bone cortex, Screwing the osseous implant by screwing in the direction of the second threading (11) to complete the screwing of the body of the threaded rod (1) into the bone and proceed with the expansion of the tubular body (2).

In some embodiments of the method, the method comprises providing an opening to allow the insertion of the implant through the cortical bone by means of a cortical preform tool. This is in particular the case when the material used to make the implant is PEEK.

In other embodiments, this perforation is not necessary due to the self-tapping notches (231).

The present application also relates to the expansion of an osseous implant in the osseous tissue.

In some embodiments, as for example represented in FIG. 3*a*, the tubular body (2) has an acute angle α at the end of its distal portion (23). This angle α opens and increases as the rod (1) enters the tubular body (2), during the expansion.

In some embodiments, as for example represented in FIG. 3*b*, the angle α, opening increasingly during the expansion, becomes an angle β, the angle β being the angle of the expanded tubular body (2).

It will be noted that in the deployed position, the walls of the tubular body (2) can in some embodiments be parallel instead of creating an angle β.

In some embodiments, the tubular body (2) has a domed shape at the central bearing point, as for example represented in FIG. 3*c*, by the presence of the angles α and β.

In some embodiments, as for example represented in FIG. 5*a*, FIG. 5*b* and FIG. 10, the implant is expandable between, on the one hand, a rest configuration in which an abutment mechanism interlocks the tubular body (2) and said rod (1)

thanks to the reversal of their two respective screw pitches and, on the other hand, an expanded configuration obtained by the actuation of said complementary internal and external threadings of the tubular body (2) and of the rod (1) mutually, causing the penetration of the rod (1) in the body tubular (2) and generating the expansion of said tubular body (2), thanks to the external diameter of the rod (1) which is greater than the internal diameter of the tubular body (2), at least on a distal portion, by deformation of the body tubular (2) during the penetration of the rod (1) in the tubular body (2).

As for example represented in FIG. 5a to FIG. 10, the external profile of the rod (1) and the internal profile of the tubular body (2) are complementary, so that in some embodiments they provide, in an expanded configuration:

A proximal bearing point supported by the complementarity of the outer diameter of the rod (1) with the inner diameter of the tubular body (2), this proximal bearing point does not cause the deformation of the tubular body (2), A distal bearing point supported by the cooperation between the tubular body (2) whose inner diameter narrows towards the distal portion until becoming smaller than the outer diameter of the rod (1), A "central" bearing point located between the two distal and proximal bearing points, formed by the cooperation between the outer diameter of the rod (1) and the inner diameter of the tubular body (2) which induce an outer diameter of the tubular body (2) at the "central" level which is greater than the outer diameter of the tubular body (2) at the proximal bearing point, said central bearing point are not necessarily located exactly in the middle of the other two bearing points.

In some embodiments, the outer diameter of the tubular body (2) at the "central" level is also preferably greater than the outer diameter of the tubular body (2) at the distal bearing point.

In some embodiments, the distal bearing point is formed by the distal portion (13) of the rod comprising a tip (17), whose external profile is complementary to the internal profile of the distal portion (23) of the tubular body (2).

In some embodiments, the distal portion (13) is stopped in translation in the direction of the external threading (21) by the mutual abutment configured in the tubular body (2), the shape of said mutual abutment and the internal shape of the tubular body (2) being configured to cause the radial expansion of the tubular body (2) when the rod (1) is screwed into the tubular body (2).

In some embodiments, the expansion of the distal portion of the implant is ensured by the cooperation between the conical or frustoconical profile of the tip (17) of the rod (1) and the internal diameter of the tubular body (2), while the expansion of the central bearing point is ensured by the cooperation between the internal diameter at the central bearing point of the tubular body (2) relative to the increase in the external diameter of the rod (1), from the mutual abutment in the direction of the proximal portion.

Preferably, this increase in the external diameter of the rod (1) is located at a predetermined distance relative to the marker (16), it is thus possible to screw the implant in the rest position up to said marker (16) and then screw in the opposite direction to allow penetration of the rod inside the sleeve followed by the expansion of the tubular body (2), while controlling the depth at which the expansion will take place.

In addition, the external diameter of the rod (1) is greater than the internal diameter of the tubular body (2), by means of at least one narrowing (271) on a distal portion (23), the external diameter of the rod (1) reaching its maximum size at the distance along the longitudinal axis (L) corresponding to the central bearing point in the extended position. Said at least one narrowing (271) is located, relative to the proximal portion and along the longitudinal axis (L), at a distance determined as a function of the depth, in the osseous tissue, at which said expansion is desired, as represented for example in FIG. 4a and FIG. 4b.

Said narrowing (271) is located at a variable distance from the tip (17).

In some embodiments, the mutual abutment mechanism includes a rib (26) protruding inside the tubular body (2), complementary to a shoulder or to a cut (172) located on the tip of the rod (1).

In some embodiments, the diameter of the rod (1) gradually increases from said shoulder or said cut (172), towards the distal portion (13) of the rod (1) to allow the central bearing point to expand the tubular body (2).

In some embodiments, the proximal bearing point is formed on at least one portion of the distal portion (23) complementary to the external profile of the rod (1). This proximal bearing point corresponds to a complementarity of diameters between the tubular body (2) and the rod (1).

In some embodiments, the "central" bearing point is formed on an intermediate portion located between the distal portion (23) and the proximal portion (22) whose internal profile is complementary to the external profile of the rod (1).

In addition, in some embodiments, a synergistic effect is observed between the mutual abutment and the "central" bearing point allowing the screwing at the start but also the bearing during the expansion.

In some embodiments, the mutual abutment mechanism further includes a rib or a shoulder of the interior of the tubular body (2), complementary to a cut or to a protrusion on the rod (1).

In some embodiments, the central bearing point includes a rib or a shoulder or a protrusion inside the tubular body (2), complementary to the external diameter of the rod (1), or a rib on the inside of the tubular body (2), complementary to a groove or to a shoulder on the rod (1).

The bearing points at the maximum expansion force guarantee non-sagging on the parts accumulating the most contact forces between the bone and the implant.

As for example represented in FIG. 3a to FIG. 3c, and FIG. 6 to FIG. 10, the distal portion (23) of the tubular body (2) in particular includes longitudinal through (24) and non-through (25) slots to allow the cylindrical expansion of the tubular body (2).

In some embodiments, the synergy between the through-slots (24) and the non-through slots (25) also allows truncated cone geometry.

In some embodiments, the expansion is allowed by thanks to at least one longitudinal through (24) or non-through (25) slot, preferably several through (24) and non-through (25) slots. It is also preferable that the distal portion (23) includes the two types of slots, that is to say longitudinal through-slots (24) and longitudinal non-through slots (25). It should be noted that the distribution of the notches (231) of the self-tapping portion (23) of the tubular body (2) depends on the number of longitudinal through (24) and non-through (25) slots. The longitudinal non-through slots (25) and the central bearing point allow the expansion of the tubular body (2).

As for example represented in FIG. 5a to FIG. 10, the tubular body (2) is expanded after penetration of the rod (1) inside the tubular body (2).

In some embodiments, the tubular body (2) expands in a cylindrical form and the longitudinal through (24) and non-through (25) slots on the distal portion (23) of the tubular body (2) allow the cylindrical expansion of the tubular body (2) by allowing elastic or plastic deformation of the tubular body (2) upon penetration of the rod (1) into the tubular body (2). The tubular body (2) can be made, for example, of titanium which has good plastic deformation properties. The longitudinal non-through slots (25) thus contribute to the stability of the osseous implant in the osseous tissue by allowing, during the expansion, to be able to maintain the contact profile on the three bearing points between the tubular body (2) and the rod (1), and by allowing the forces due to the expansion to be uniformly distributed over the periphery of the expanded tubular body (2).

In some embodiments, the through-slots (24) and the non-through slots (25) are disposed offset relative to each other over the length, this offset disposition allows improving the flexibility and the mechanical strength of the tubular body (2) during the expansion.

Finally, in some embodiments, the non-through slots (25) allow the tubular body (2) to expand in the cancellous osseous tissue by presenting a domed shape, of the convex type, making it possible to compress and densify the material over its periphery, thus improving primary stability, healing, and making it possible to avoid the addition of cement to stabilize and immobilize the osseous implant.

The osseous implant proposed in the invention can therefore be implanted quickly and accurately in the osseous tissue, and remain implanted in a very stable manner in the osseous tissue.

The present application describes various technical characteristics and advantages with reference to the figures and/or to various embodiments. Those skilled in the art will understand that the technical characteristics of a given embodiment can indeed be combined with characteristics of one or more other embodiment(s) unless the reverse is explicitly mentioned or these characteristics are incompatible or the combination does not work.

More generally, combinations of various types of implant retaining means and/or spine retaining means are envisaged and will be appreciated by those skilled in the art using the functional and structural considerations provided in the present application. In addition, the technical characteristics described in a given embodiment can be isolated from the other characteristics of this mode unless the reverse is explicitly mentioned, in particular because the functional considerations provided in the present application will provide a sufficient explanation so that the structural adaptations possibly necessary are within the reach of those skilled in the art.

Those skilled in the art, upon reading the present application, will understand that embodiments in many specific forms other than those described in detail are possible without departing from the field of application of the invention as claimed. Therefore, the present embodiments should be considered by way of illustration, but can be modified in the field defined by the scope of the appended claims, and the invention should not be limited to the details given above.

The invention claimed is:

1. An osseous anchoring implant with optimized expansion, comprising:
   a tubular body extending between a proximal portion having a first internal diameter, and a distal portion having a second internal diameter smaller than said first internal diameter, these two portions defining a longitudinal axis and said first and second internal diameters defining an internal profile of said tubular body, and comprising at least a first threading inside the tubular body and, at least a second threading outside the tubular body,
   a rod extending between a proximal portion and a distal portion on an axis collinear with the longitudinal axis and having, along said longitudinal axis, an external profile complementary to said internal profile of said tubular body and, at least one external threading whose screw pitch is reversed relative to said second external threading of the tubular body,
   the implant being expandable between a rest configuration in which an abutment mechanism interlocks said tubular body and said rod thanks to the reversal of these two screw pitches and, an expanded configuration obtained by the actuation of said complementary internal and external threadings of the tubular body and of the rod mutually, causing the penetration of the rod into the tubular body and generating the expansion of said tubular body, thanks to the external diameter of the rod which is greater than the internal diameter of the tubular body, at least on a distal portion, by deformation of the tubular body during penetration of the rod into the tubular body, wherein
   the external profile of the rod and the internal profile of the tubular body are complementary, so that they provide, in an expanded configuration:
      a proximal bearing located at the proximal portion of the rod, the proximal bearing being supported by the complementarity of the outer diameter of the rod with the inner diameter of the tubular body in such a way that the tubular body shape remains constant at the level of the proximal bearing,
      a distal bearing located at the distal portion of the rod, the distal bearing being supported by the cooperation between the rod and the tubular body in such a way that the inner diameter of the tubular body narrows towards the distal portion until becoming smaller than the outer diameter of the rod at the level of the distal bearing,
      a central bearing located between the proximal and distal bearings, the central bearing being formed by the cooperation between the outer diameter of the rod and the inner diameter of the tubular body comprising a rib or a shoulder or a protrusion inside the tubular body complementary to the external diameter of the rod, in such a way that, when the rod penetrates into the tubular body during said expansion, the outer diameter of the tubular body, at the level of the central bearing is greater than the outer diameter of the tubular body at the level of the proximal bearing.

2. The implant according to claim 1, wherein the proximal bearing is formed on at least one portion of the proximal portion of the tubular body complementary to the external profile of the rod.

3. The implant according to claim 2, wherein the distal bearing is formed by the distal portion of the rod comprising a tip whose external profile is complementary to the internal profile of the distal portion of the tubular body.

4. The implant according to claim 3, wherein the central bearing is formed on an intermediate portion of the tubular body located between the distal portion of the tubular body and the proximal portion of the tubular body whose internal profile is complementary to the external profile of the rod.

5. The implant according to claim 3, wherein the abutment mechanism includes a rib protruding inside the tubular body complementary to a shoulder or to a cut located on the tip of the rod.

6. The implant according to claim 5, wherein the central bearing further includes a rib on the inside of the tubular body, complementary to a groove or to a shoulder on the rod.

7. The implant according to claim 6, wherein the central bearing and the abutment mechanism interlocking the tubular body and the rod are formed by the same structure.

8. The implant according to claim 1, wherein the internal diameter of the tubular body comprises, at the distal portion, at least a shrinkage having a size inferior to the external diameter of the rod.

9. The implant according to claim 8, wherein said at least one shrinkage is located at a distance from the proximal portion, along the longitudinal axis, determined as a function of the depth, in the osseous tissue, at which the expansion of the tubular body is desired.

10. The implant according to claim 1, wherein the distal portion of the tubular body comprises a frustoconical portion whose internal diameter is smaller than the external diameter of the rod.

11. The implant according to claim 8, wherein the frustoconical portion has a threading with a conical core allowing the tubular body to sink deep into the bone.

12. The implant according to claim 1, wherein the distal portion of the tubular body includes self-tapping notches.

13. The implant according to claim 12, wherein the distal portion of the tubular body includes longitudinal through-slots allowing the expansion of the tubular body.

14. The implant according to claim 13, wherein there are as many self-tapping notches as there are longitudinal through-slots.

15. The implant according to claim 10, wherein the distal portion of the tubular body includes longitudinal non-through slots allowing the expansion of the tubular body.

16. The implant according to claim 1 wherein said rod comprises at least one distance marker to visualize the moment when the screwing of the rod in the tubular body must be carried out in the opposite direction to the screwing of the tubular body into the osseous tissue.

17. The implant according to claim 16, wherein said at least one distance marker is a laser marker.

18. A method for placing an implant according to claim 1, the method comprising the following steps:
    screwing the implant in the direction of the external threading of the tubular body until the distance marker is flush with the surface of the bone cortex; and
    screwing the implant by screwing in the direction of the threading of the rod to complete the screwing of the body of the threaded rod into the bone and to proceed with the expansion of said tubular body.

19. The implant placing method according to claim 18, wherein a cortical bone is perforated by means of a cortical preform tool.

20. A method for extracting an implant according to claim 1, the method comprising the following steps:
    unscrewing the implant in the direction of the external threading until the appearance of a distance marker;
    locking the implant by a clamp blocking the rod in the tubular body in the rest position; and
    unscrewing the implant in the direction of the second threading.

21. An extraction method according to claim 20, the method comprising an additional screwing before unscrewing the implant.

* * * * *